United States Patent [19]

Blount

[11] 4,107,140

[45] Aug. 15, 1978

[54] PRODUCTION OF THE REACTION PRODUCTS OF OXIDATED SILICON COMPOUNDS REACTING WITH ORGANIC MONOHYDROXY COMPOUNDS

[76] Inventor: David H. Blount, 5450 Lea St., San Diego, Calif. 92105

[21] Appl. No.: 854,843

[22] Filed: Nov. 25, 1977

Related U.S. Application Data

[63] Continuation-in-part of Ser. No. 765,050, Feb. 2, 1977, Pat. No. 4,089,883, which is a continuation-in-part of Ser. No. 703,925, Jul. 9, 1976, abandoned, and Ser. No. 589,626, Jun. 23, 1975, abandoned.

[51] Int. Cl.² ............................................. C08G 77/04

[52] U.S. Cl. ............................... 521/154; 260/824 R; 528/28; 528/29; 528/14

[58] Field of Search .................... 260/2.5 AB, 2.5 AC, 260/2.5 R, 824 R, 46.5 E

[56] References Cited

U.S. PATENT DOCUMENTS 4,069,391  1/1978  Blount ......................... 260/46.56 UX Primary Examiner—Paul F. Shaver

[57] ABSTRACT

A fine granular oxidated silicon compound will react chemically with organic monohydroxy compounds in the presence of an alkali catalyst to produce organic silicate compounds.

20 Claims, No Drawings

PRODUCTION OF THE REACTION PRODUCTS OF OXIDATED SILICON COMPOUNDS REACTING WITH ORGANIC MONOHYDROXY COMPOUNDS

CROSS-REFERENCE TO RELATED APPLICATIONS

This application is a continuation-in-part of my co-pending U.S. Patent application Ser. No. 765,050, filed Feb. 2, 1977, now U.S. Pat. No. 4,089,883, which is a continuation-in-part of U.S. patent application Ser. No. 703,925, filed Jul. 9, 1976, now abandoned and U.S. patent application Ser. No. 589,626, filed Jun. 23, 1975, now abandoned.

BACKGROUND OF THE INVENTION

This invention relates to a process for the production of organic silicate compounds by chemically reacting a fine granular silicon acid and silica with organic monohydroxy compounds by heating the mixture in the presence of an alkali catalyst.

The silicon acid compounds used in this process may be produced by the chemical reaction of a dry alkali metal metasilicate with a hydrogen containing acid salt or a concentrated mineral acid. The white granular silicon acid is washed with water, filtered and then air dried at 25° to 75° C. The white granular silicon acid was analyzed by Infrared analysis, using IR KBr disc method. The infrared analysis was very similar to that obtained with Mallinckrodt's hydrated silica except for the area which shows the presence of Si-H bonds. The silicon acids contain a mixture of silicoformic acid and hydrated silica.

The hydrated silica and silica may be produced by any of the commonly known methods. It is preferred that the silicoformic acid, hydrated silica and silica be in the form of fine granules or powder.

The exact course of the reactions which take place during the process to produce organic silicate compounds cannot be determined with 100% certainty.

Organic silicate compounds may be used as a filler in elastomers, phenol resins, urea resins, molding powders, pigments, as an anit-caking agent, as a flatting agent for paints, lacquers and organic coating agents, and in the manufacturing of soap and detergents. The organic silicate compounds may be reacted chemically with polyisocyanates and polyurethane prepolymers.

SUMMARY OF THE INVENTION

I have discovered that silicoformic acid, hydrated silica and silica will react chemically with a monohydroxy organic compound in the presence of a small amount of an alkali catalyst at a temperature of the monohydroxy organic compound to produce an organic silicate compound.

Various alkali catalysts such as alkali metal carbonates, hydroxides, such as alkali metal carbonates, hydroxides, oxides and alkali metal salts of weak acids may be used as the catalyst in the chemical reaction to produce organic silicate compounds. The most useful alkali metal carbonate is sodium carbonate, but other alkali metal carbonates such as potassium carbonate may be used. Sodium and potassium hydroxide are the most useful alkali metal hydroxides. Sodium silicate may also be used as the catalyst. Best results are obtained when the alkali catalyst is added in the amount of 1 to 10% of the weight of the oxidated silicon compound.

The alkali catalyst is necessary in this process, because when a monohydroxy organic compound is heated with silicoformic acid, hydrated silica or silica without an alkali catalyst, no organic silicate compound is produced.

Various monohydroxy compounds may be used such as methanol, ethanol, propanol, isopropyl alcohol, butanol, pentanol, ethylene chlorohydrin, amyl alcohol, hexyl alcohol, octyl alcohol, nonyl alcohol, decyl alcohol, lauryl alcohol, cetyl alcohol, isoamyl alcohol, capric alcohol, hydroxyacetic acid, lactonitrile, lactic acid, glycolic acid, hydroxylbutyric acid, hydroxycaproic acid, hydroxypropionic acid, hydroxy nitriles, other hydroxy acids, monothioalcohol, monothiophenol, cyclohexanol, methylcyclohexanol, benzyl alcohol, cyclohexano-methanol, methallyl alcohol, and mixtures thereof.

The various organic silicate compounds produced by this invention are soluble in alkali metal hydroxide aqueous solutions such as sodium hydroxide and potassium hydroxide. These solutions may be used as adhesives for paper, reacted with polyisocyanate compounds and isocyanate-terminated liquid polyurethane propolymers to produce solid and fine cellular solid polyurethane silicate products.

The organic silicate compounds produced by this invention will react chemically with a wide variety of polyisocyanate compounds and polyurethane prepolymers to produce urethane silicate prepolymers and poly(urethanesilicate) foams and resins. Suitable polyisocyanates such as tolylene, metaphenylene, 4-chlorophenylene-1,3-; methylene bis-(phenylene-4-); bisphenylene-4,4'-; 3,3'-dimethoxy-biphenylene-4,4'-; 3,3'-diphenylbiphenylene-4,4'; naphthalene-1,5 and tetrahydronaphthalene-1,5-dissocyanates and triphenylmethane triisocyanate; alkylene polyisocyanates such as ethylene, ethylidene; propylene-1,2-; butylene-1,4-; butylene-1,3-; hexylene-1,6-; decamethylene-1,10-; cyclohexylene-1,2-; cyclohexylene-1,4-; and methylene bis (cyclohexyl-4,4'-) diisocyanates.

Toluene diisocyanates are preferred, especially a mixture of 80% of the 2,4-isomer and 20% of the 2,6-isomer thereof. Inorganic polyisocyanates, polyisothiocyanates and a phosgenation product of anilineformaldehyde condensation are also suitable according to this invention.

The listed polyisocyanates may be first reacted in molar excess with hydroxyl-containing or carboxyl-containing polyesters, polyethers, polysulfides, polybutadienes and other polyols to produce isocyanate-terminated liquid polyurethane prepolymer, as is known in the art. These liquid isocyanate-terminated liquid polyurethane prepolymers will react chemically with the organic silicate in the presence of a catalyst such as water to produce a polyurethane silicate solid or fine cellular solid.

Plasticizers, fillers, curing rate modifiers, pigments, extenders and the like may be added to the polyurethane prepolymer or at the time of curing and may be in the amount from 5 to 50% by weight, based on the weight of the reactants. Plasticizers may include benzoate ester, phthalate esters, dipropylene glycol benzoate, dodecyl phthalate, propylene glycol phthalate and mixtures thereof. Extanders may include high boiling coal tar distillates, mineral oils, poly(alphamethyl styrene) polymers, mercapto-terminated liquid polysulfide polymers and mixtures thereof.

Various catalysts may be utilized to cure the polyisocyanate silicate prepolymer and to produce poly(urethane silicate) solid and fine cellular solids such as water, aqueous magnesium hydroxide, aqueous sodium silicate, aqueous suspension of hydrated silica and silica, acetic acid, N-methylmorphatine, dimethyl ethanolamine, triethylamine, N-N'-diethylcyclohexylamine, N-N'-diethycyclohexylamine; N,N'-dimethylcyclohexylamine, organic tin compounds and mixtures thereof. Water, together with an amine and/or a tin compound catalyst, has been found to be especially effective and is therefore preferred. The catalyst is used in the amount of 3 to 40% by weight, based on the weight of the mixture of organic silicate and polyisocyanate silicate and/or isocyanate-terminated liquid polyurethane prepolymer.

If desired, suitable amounts of modifiers such as alkalated phenoxy, polyethoxy, ethanol, ammonium oleate, sulphenated castor oil, manganous chloride, zinc stearate, paraffin oil, calcium stearate, dioctyl sulfosuccinate and mixtures thereof, may be added to modify the characteristics of the urethane silicate resins and fine cellular solids.

If desired, special purpose additives, (5 to 50% by weight) such as plasticizers, fillers, curing rate modifiers, pigments and the like may be added to the urethane silicate prepolymer such as high-boiling aromatic ester plasticizers, coal tars, mineral oil, poly(alpha-methyl styrene) polymer and mercapto-terminated liquid polysulfide polymers.

The poly(isocyanate silicate) resins and poly(urethane silicate) resins produced by this invention may be produced as non-porous or cellular products. The non-porous products may be rigid or elastic; the cellular products may be rigid, semi-rigid, or soft. The products have good flame retardant properties. The poly(isocyanate silicate) resins and poly(urethane silicate) resinous products may be used for insulation, floatation in boats and structural applications.

For the purpose of this invention, the product produces by reacting silicoformic acid, hydrated silica or silica with a monohydroxy organic compound will be generally identified as "organic silicate compound." The reaction product of the organic silicate compound with a polyisocyanate will generally be identified as "poly(isocyanate silicate) prepolymer or product." The reaction product of organic silicate compound with isocyanate-terminated liquid urethane propolymers will be generally identified as "poly(urethane silicate)" products.

An aqueous solution of the organic silicate compounds as produced in this invention may be produced by mixing 8 parts by weight of the organic silicate compound with 2 to 3 parts by weight of sodium hydroxide flakes or potassium hydroxide pellets in 20 to 40 parts by weight of water. The mixture is heated to 60° to 100° C for a few minutes while agitating until a clear solution is produced.

The aqueous solution of organic silicate may be mixed with a polyisocyanate compound or with a isocyanate-terminal liquid prepolymer in the ratio of 10 to 100%, percentage based on the weight of the isocyanates, to produce a solid or fine cellular solid product which may be used for insulation, as a coating agent for wood, floatation in boats and structural applications. There is a reduction in the cost of producing urethane foams by utilizing the aqueous solution of organic silicate compound. It also improves the flame resistant properties. Various polyols, polyesters and polyethers may be added to the aqueous solution of organic silicate compounds to improve the final urethane silicate product.

The preferred method to react the monohydroxy organic silicate reaction products produced in this invention with a polyisocyanate compound is to mix about 2 parts by weight of the monohydroxy organic silicate reaction product with 1 to 6 parts by weight of the polyisocyanate compound. The mixture is then heated to 20° to 60° C while agitating for 10 to 20 minutes, thereby producing a poly(isocyanate silicate) prepolymer. A catalyst, such as water, is then thoroughly mixed with the polyisocyanate silicate prepolymer, the chemical reaction starts in a few minutes, and the reaction is complete in 10 minutes to 2 hours, thereby producing a solid or a fine cellular solid product. In some products, it is necessary to further heat at 70° to 100° C for 1 to 2 hours to complete the curing process.

The preferred method to cure the poly(isocyanate prepolymer) is to react it with an aqueous solution of the monohydroxy organic silicate reaction product. It is reacted by thoroughly mixing it in the ratio of 0.01 to 2 parts by weight of the solution of the organic silicate with about 1 part by weight of the poly(isocyanate silicate) prepolymer. The mixture is cured in 10 minutes to 2 hours, therby producing a solid or a fine cellular solid product.

The preferred method to react the monohydroxy organic silicate reaction product (organic silicate) in this invention with a isocyanate-terminated liquid polyurethane prepolymer is to mix thoroughly in the ratio of 1 part by weight of the polyurethane prepolymer, then add a catalyst, such as water in the amount of 3 to 40% by weight or an aqueous solution of the monohydroxy organic silicate reaction product (containing 10 to 50% by weight of the organic silicate compound) in the amount of 10 to 200% by weight, percentage based on the weight of the reactants. The mixture is cured in 10 minutes to 2 hours, thereby producing a poly(urethane silicate) solid product. In some products further heating at 70° to 100° C for 1 to 2 hours is required to complete the curing process.

Polyol compound may be added to the curing catalyst in the amount of 10 to 40% by weight, percentage based on the weight of the curing catalyst. The polyol compounds may also be reacted with the oxidated silicon compound along with the monohydroxy compound. The polyol compound may be selected from the group consisting of glycerol, glycerol monochlorohydrin, ethylene glycol, propylene glycol, butylene glycol, trimethylene glycol, tetramethylene glycol, pentamethylene glycol, hexamethylene glycol, diethylene glycol, triethylene glycol, dipropylene glycol, tetraethylene glycol, polyethylene glycol, polypropylene glycol, ether glycols, Bisphenol A, resorcinol, bis(beta-hydroxyethyl) terephthalate, 2-ethyl-2-(hydroxymethyl)-1,3-propanediol, pentaerythritol, di and tripentaerythritol, trimethol propane, trimethol ethane, 2,2'-oxydiethanol, glucose, mannose, fructose, molasses, can sugar, dextrines, starches, corn syrup, maple syrup, castor oil, monoglycerides, polyester polymers with free hydroxyl groups and mixtures thereof.

The primary object of the present invention is to produce organic silicate compounds. Another object is to produce organic silicate compounds which will react chemically with diisocyanates to produce useful resins and foams. A further object is to produce organic silicate compounds which may be used as a filler in paints, varnishes and molding powders. Still another object is to produce aqueous solutions of organic silicate compounds which will react with polyisocyanates and isocyanate-terminated liquid polyurethane prepolymers to produce solid/fine cellular solid products.

DESCRIPTION OF PREFERRED EMBODIMENTS

My invention will be illustrated in greater detail in the specific examples which will follow, it being understood that these preferred embodiments illustrate, but do not limit the procedures which may be used in the production of the reaction products of oxidated silicon compounds reacting with organic monohydroxy compounds and their resinous products. Parts and percentages are by weight unless otherwise indicated.

EXAMPLE 1

Dry granular sodium metasilicate pentahydrate is gradually mixed with concentrated sulfuric acid in the ratio of about 1 to 1 mols. Oxygen evolves from the mixture and the chemical reaction is complete in 2 to 4 hours, thereby producing a granular mixture of silicoformic acid, hydrated silica and sodium sulfate. The mixture is washed with water then filtered to remove the sodium sulfate then air dried at 25° to 85° C into a fine white granular mixture of silicon acids.

About 1 part by weight of the fine granular silicon acids, 2 parts by weight of ethyl alcohol and 1 to 10%, percentage based on the weight of the silicon acids, of sodium carbonate are mixed then heated to just below the boiling temperature of ethyl alcohol (50° to 80° C) for 20 to 60 minutes, thereby producing a light tan granular organic silicate compound, ethyl silicate.

Ethyl silicate is soluble in dilute sulfuric acid and dilute sodium hydroxide aqueous solution.

EXAMPLE 2

An aqueous solution of sodium silicate is neutralized with an acid, dilute sulfuric acid, by adding the acid until the aqueous solution of sodium silicate gels. The silica hydrogel is then washed with water, filtered then air dried at ambient temperature, thereby producing a fine granular hydrated silica.

About 1 part by weight of fine granular hydrated silica, 2 parts by weight of butyl alcohol and 1 to 10% by weight of potassium carbonate are mixed. The mixture is heated to just below the boiling point of butyl alcohol while agitating at ambient pressure for 20 to 60 minutes, thereby producing a white granular organic silicate compound, butyl silicate.

The butyl silicate is soluble in dilute sulfuric acid and dilute sodium hydroxide solution.

EXAMPLE 3

About 1 part by weight of fine granular hydrated silica, 3 parts by weight of caprylic alcohol and 10% by weight of sodium carbonate, percentage based on the weight of hydrated silica, are mixed. The mixture is then heated to just below the boiling temperature of caprylic alcohol while agitating at ambient pressure for 20 to 60 minutes, thereby producing a white granular organic silicate compound, caprylic silicate.

The caprylic silicate floats on water. It is soluble in warm dilute sodium hydroxide solution, and this solution is very useful as an adhesive to produce paper products.

EXAMPLE 4

About 1 part by weight of hydrated silica in a dry fine granular form, 1 to 2 parts by weight of methyl alcohol and 1 to 10% by weight of sodium hydroxide flakes, percentage based on the weight of hydrated silica, are mixed in a closed system such as an autoclave then heated to just below the boiling point of methyl alcohol at ambient to 60 psig of pressure while agitating for 20 to 60 minutes, thereby producing a fine granular organic silicate compound, methyl silicate.

EXAMPLE 5

About 1 mol of sodium metasilicate pentahydrate, 1 mol of concentrated sulfuric acid and 2 mols of propyl alcohol are slowly mixed until the pH is 7 to 8, then agitated while keeping the temperature below the boiling temperature of propyl alcohol for 20 to 60 minutes, thereby producing a mixture of sodium sulfate, organic silicate compounds (propyl silicate and dipropyl silicate) and hydrated silica. The mixture is then washed with water and filtered to remove the sodium sulfate, thereby recovering the organic silicate compounds.

EXAMPLE 6

One part by weight of the silicon acids as produced in Example 1, 2 parts by weight of ethylene chlorohydrin and 10% by weight of potassium hydroxide are mixed. The mixture is then heated to fust below the boiling temperature of ethylene chlorohydrin while agitating at ambient pressure for 20 to 60 minutes, thereby producing fine granular organic silicate compound, chloroethylene silicate.

The chloro-ethylene silicate is soluble in dilute sulfuric acid and dilute sodium hydroxide aqueous solution.

EXAMPLE 7

About 1 part by weight of fine granular hydrated silica, 2 parts by weight of glycolic acid and 10% by weight, percentage based on weight of hydrated silica, of sodium carbonate are mixed. The mixture is then heated to just below the boiling temperature of glycolic acid while agitating for 20–60 minutes at ambient pressure, thereby producing an organic silicate compound, glycolic acid silicate.

EXAMPLE 8

About 1 part by weight of fine granular hydrated silica, 2 parts by weight of allyl alcohol, and 1% by weight, percentage based on weight of hydrated silica, of potassium hydroxide are mixed. The mixture is then heated in a closed system to just below the boiling temperature of allyl alcohol while agitating at ambient to 60 psig of pressure for 20 to 60 minutes, thereby producing an organic silicate compound, allyl silicate and diallyl silicate.

EXAMPLE 9

About 1 part by weight of fine granular silica, 2 parts by weight of furfuryl alcohol, 1 to 10% by weight of potassium hydroxide and 3 parts by weight of water are mixed. The mixture is then heated to just below the boiling temperature of furfuryl alcohol while agitating for 20 to 60 minutes, thereby producing an organic silicate compound, furfuryl silicate.

The furfuryl silicate is polymerized by mixing in an acid until the pH is 3 to 6, thereby producing poly(furfuryl silicate) polymer.

EXAMPLE 10

A polyurethane prepolymer was prepared by reacting toluene diisocyanate (80% 2,4- and 20% 2,6-) with polypropylene glycol (500 to 750 mol wt.) in molar ratio of about 2:1. 4 parts by weight of the prepolymer are thoroughly mixed with 1 part by weight of ethyl silicate as produced in Example 1, and then a catalyst, an aqueous solution of ethyl silicate in dilute sodium hydroxide (40% by weight of ethyl silicate and 10% by weight of sodium hydroxide flakes), in the amount of 1 part per 2 parts by weight of the polyurethane prepolymer, is added and thoroughly mixed. The polyurethane prepolymer is cured in 10 to 60 minutes, thereby producing a tough solid poly(urethane silicate) product.

EXAMPLE 11

A polyurethane prepolymer was prepared by reacting 0.75 mol of ethylene glycol, 0.25 mol of propylene glycol and 1 mol of adipic acid to produce a polyester polymer, having a molecular weight of about 1800. The polyester was reacted with toluene diisocyanate to produce a polyurethane with an NCO content of about 4%. About 4 parts by weight of said prepolymer are mixed with 1 part by weight of propyl silicate as produced in Example 5, then about 1 part by weight of a catalyst, containing about 40% by weight of said propyl silicate, 10% by weight of potassium hydroxide and 50% by weight of water, is added. The mixture is thoroughly mixed and is cured in about 12 hours to produce a tough elastomer.

EXAMPLE 12

A liquid hydroxyl-terminated polybutadiene is reacted with toluene diisocyanate to produce a polyurethane prepolymer with a free NCO content of about 4%; then 4 parts by weight of the prepolymer is mixed with 2 parts by weight of caprylic silicate compound as produced in Example 3; then a catalyst, water, containing a small amount of stannous octoate, in the amount of 10% by weight, percentage based on the weight of the reactants, is added and thoroughly mixed, thereby producing a solid poly(urethane silicate) product.

EXAMPLE 13

About 1 part by weight of ethyl silicate as produced in Example 1 and 2 parts by weight of toluene diisocyanate (80% 2,4-isomer and 20% 2,6-isomer) are mixed then agitated while heating to 20° to 60° C for 10 to 20 minutes thereby producing polyisocyanate silicate prepolymer.

About 1 part by weight of a catalyst, an aqueous solution containing 30% by weight of ethyl silicate, 6% sodium hydroxide flakes and 44% water, is added to about 2 parts by weight of said polyisocyanate silicate prepolymer are thoroughly mixed, and in 3 to 10 minutes the mixture begins to expand, thereby producing a polyisocyanate silicate fine cellular product. It expands 4 to 6 times its original volume to produce a rigid fine cellular product.

EXAMPLE 14

About 1 part of chloroethylene silicate as produced in Example 6 and 1.5 parts by weight of toluene diisocyanate are mixed then heated to 20° to 60° C while agitating for 10 to 20 minutes, thereby producing a polyisocyanate silicate prepolymer.

A curing catalyst, is produced by mixing one part by weight of chloroethylene silicate, 0.25 parts by weight of sodium hydroxide flakes and 1 part by weight of water are mixed then heated while agitating to 60° to 80° C for a few minutes until a clear solution of chloroethylene silicate is produced. One part by weight of said curing catalyst is mixed with 0.25 parts by weight of glycerol and 2 parts by weight of said polyisocyanate silicate prepolymer then agitated for a few minutes until the mixture begins to expand. The mixture expands 6 to 10 times its original volume, thereby producing a rigid, fine cellular solid poly(isocyanate silicate) product.

EXAMPLE 15

About 1 part by weight of fine granular silica, 10% by weight of sodium hydroxide flakes, percentage based on weight of silica, 1 part by weight of amyl alcohol, 1 part by weight of glycerol and 2 parts by weight of water are mixed then heated to just below the boiling temperature of the alcohols while agitating at ambient pressure for 20 to 60 minutes, thereby producing a mixture of amyl silicate and glycerol silicate.

About 1 part by weight of toluene diisocyanate and 2 parts by weight of the mixture of amyl silicate and glycerol silicate are mixed then heated to 20° to 60° C while agitating at ambient pressure for 10 to 20 minutes, thereby producing polyisocyanate silicate prepolymer.

1 part by weight of water containing 10% sodium dioctyl sulfosuccinate is mixed thoroughly with said polyisocyanate silicate prepolymer, and the mixture begins to expand in 5 to 15 minutes. It expands 8 to 10 times its original volume, thereby producing a rigid fine cellular, solid poly(isocyanate silicate) product.

The poly(isocyanate silicate) product is soluble in organic solvents such as glacial acetic acid and may be painted on wood to produce a tough, clear, protective coating. The cellular product may be used for floatation in boats, for insulation and structural applications.

EXAMPLE 16

About 1 part by weight of ethylene chlorohydrin, 1 part by weight of glycolic acid, 1 part by weight of fine granular hydrated silica and 0.1 part by weight of sodium carbonate are mixed then heated to just below the boiling temperature of the reactants while agitating at ambient temperature for 20 to 60 minutes, thereby producing a mixture of chloroethylene silicate and glycolic acid silicate.

About 2 parts by weight of the mixture of chloroethylene silicate and 2 parts by weight of toluene diisocyanate (80% 2,4-isomer and 20% 2,6-isomer) are mixed then heated to a temperature of 20° to 60° C while agitating at ambient pressure for 10 to 20 minutes, thereby producing poly(isocyanate silicate) prepolymer.

About 1 part by weight of the poly(isocyanate silicate) prepolymer is mixed with 10 to 100% by weight, percentage based on the weight of the poly(isocyanate silicate) prepolymer, of an aqueous solution of an alkali metal silicate containing 20 to 60% by weight of sodium silicate or potassium silicate, thereby producing a rigid fine cellular, solid poly(isocyanate silicate) product.

EXAMPLE 17

1 part by weight of fine granular silica, 1 part by weight of ethylene chlorohydrin, 0.2 parts by weight of sodium hydroxide flakes and 2 parts by weight of water are mixed then heated to just below the boiling temperature of ethylene chlorohydrin while agitating for 20 to 60 minutes, thereby producing ethylene glycol silicate.

1 part by weight of ethylene glycol silicate containing 10% by weight of water and 1 part by weight of toluene diisocyanate are thoroughly mixed. In 5 to 15 minutes the mixture expands 6 to 10 times its original volume to produce a rigid, fine cellular solid poly(isocyanate silicate) product.

EXAMPLE 18

About 1 part by weight of ethylene silicate as produced in Example 1, 0.25 parts by weight of sodium hydroxide and 1 part by weight of water are mixed then heated to 70° to 100° C for 5 to 10 minutes until the solution is clear.

About 1 part by weight of said aqueous ethylene silicate solution is mixed thoroughly with 2 parts by weight of an isocyanate-terminated liquid polyurethane prepolymer containing 2 parts by weight of toluene diisocyanate (80% 2,4-isomer and 20% 2,6-isomer) and 1 part by weight of polyethylene glycol (450 to 500 molecular weight). The mixture begins to expand in 5 to 15 minutes and expands 8 to 10 times its original volume, thereby producing a rigid, cream-colored, cellular solid poly(urethane silicate) product.

EXAMPLE 19

About 1 part by weight of caprylic silicate as produced in Example 3, 0.2 parts by weight of potassium hydroxide and 2 parts by weight of water are mixed and then agitated until the caprylic silicate goes into solution.

About 1 part by weight of said aqueous caprylic silicate solution is mixed thoroughly with 3 parts by weight of an isocyanate-terminated liquid polyurethane prepolymer, containing 1 part by weight of castor oil and 1 part by weight of toluene diisocyanate (80% 2,4-isomer and 20% 2,6-isomer). The mixture begins to expand in 5 to 15 minutes and expands 6 to 8 times its original volume, thereby producing a white, tough, semi-rigid poly(urethane silicate) fine cellular solid product.

EXAMPLE 20

About 1 part by weight of butyl silicate as produced in Example 2, 0.25 parts by weight of sodium hydroxide flakes, and 3 parts by weight of water are mixed then heated to 70° to 100° C until the butyl silicate goes into solution.

About equal parts by weight of a polyester polymer, having about 2000 to 2200 molecular weight and produced by condensation of a mixture of about 70% ethylene glycol and 30% propylene glycol with equimolar amounts of adipic acid, was reacted with tolylene diisocyanate to produce a polyurethane prepolymer having an NCO content of about 3.5%.

About 1 part by weight of said aqueous solution of butyl silicate and 4 parts by weight of said polyurethane prepolymer are mixed thoroughly. The mixture cures in 12 to 24 hours, thereby producing a white, tough, poly(urethane silicate) elastomer.

EXAMPLE 21

About 1 part by weight of ethylene glycol silicate as produced in Example 17, 0.1 part by weight of sodium hydroxide flakes and 1 part by weight of water are mixed, thereby producing a clear solution.

A polyester, containing 4 mols of glycerol, 2.5 mols of adipic acid and 0.5 mols of phthalic anhydride are mixed with equal proportions of tolylene diisocyanate to produce a polyurethane prepolymer.

About 1 part by weight of the polyurethene prepolymer and about 1 part by weight of said aqueous solution of ethylene glycol, containing 2% by weight of zinc stearate, 0.05% paraffin oil, are thoroughly mixed. The mixture begins to expand in 5 to 15 minutes and expands 8 to 10 times its original volume, thereby producing a tough, rigid, fine cellular solid poly(urethane silicate) product.

EXAMPLE 22

A polyurethane prepolymer, produced by the reaction of a liquid hydroxyl-terminated polybutadiene with 2,4-tolylene diisocyanate and which has free NCO content of about 4% and an aqueous solution containing 5 to 15% by weight of sodium hydroxide and 20 to 60% amyl silicate as produced in Example 15, are mixed thoroughly in the ratio of 2 to 1. The mixture is cured in 12 to 24 hours, thereby producing a solid poly(urethane silicate) elastomer product. The product is further cured by heating at 70° to 80° C for 3 to 4 hours.

EXAMPLE 23

Polypropylene glycol, having an average molecular weight of 450 to 500 is reacted with toluene diisocyanate in an NCO/OH molar ratio of about 2:1, thereby producing a liquid polyurethane prepolymer and poly(alpha-methyl styrene) polymer are mixed. The aqueous solution of ethylene silicate as produced in Example 18 in the amount of 1 part by weight is mixed with 3 parts by weight of said mixture and then 1 part by weight of a liquid polysulfide polymer is added then mixed thoroughly, and the mixture cures in a short period of time, thereby producing a white solid elastomer.

Although specific materials and conditions were set forth in the above Examples, these were merely illustrative of preferred embodiments of my invention. Various other compositions, such as the typical materials listed above may be used where suitable. The reactive mixtures and products of my invention may have other agents added thereto to enhance or otherwise modify the reaction and products.

Other modifications of my invention will occur to those skilled in the art upon reading my disclosure. These are intended to be included within the scope of my invention, as defined in the appended claims.

I claim:

1. The process for the production of the reaction products oxidated silicon compounds with an organic monohydroxy compound by the following steps:
   (a) mixing about 1 part by weight of an oxidated silicon compound with 1 to 3 parts by weight of an organic monohydroxy compound;
   (b) adding an alkali catalyst in the amount of 1% to 10% by weight, percentage based on the weight of the oxidated silicon compound;
   (c) heating said mixture to just below the boiling temperature of the monohydroxy compound while agitating at ambient to 60 psig of pressure for 20 to 60 minutes, thereby
   (d) producing an organic silicate compound.

2. The process of claim 1 wherein the oxidated silicon acid is selected from the group consisting of silicoformic acid, hydrated silica and silica.

3. The process of claim 1 wherein the monohydroxy compound is selected from the group consisting of methanol, ethanol, propanol, isopropyl alcohol, butanol, pentanol, hexanol, allyl alcohol, furfuryl alcohol, ethylene chlorohydrin, amyl alcohol, hexyl alcohol, octyl alcohol, nonyl alcohol, decyl alcohol, lauryl alcohol, hydroxyacetic acid, lactonitride, lactic acid, glycolic acid, hydroxybutyric acid, hydroxycaproic acid, hydroxy propionic acid, hydroxy nitriles, hydroxy acids and mixtures thereof.

4. The product, organic silicate compounds, as produced by the process of claim 1.

5. The process of claim 1 wherein additional steps are taken after step (d) to produce a poly(isocyanate silicate) solid/fine cellular solid product by the following steps:
 (e) mixing about 1 part by weight of the organic silicate compound as produced in claim 1 and 1 to 6 parts by weight of a polyisocyanate;
 (f) heating to 20° to 60° C while agitating for 10 to 20 minutes, thereby
 (g) producing a poly(isocyanate silicate) prepolymer;
 (h) adding a curing catalyst in the amount of 0.01 to 2 parts by weight to 1 part by weight of the poly(isocyanate silicate) prepolymer, then thoroughly mixing, thereby
 (i) producing poly(isocyanate silicate) solid/fine cellular solid product.

6. The process of claim 5 wherein the polyisocyanate compound is selected from the group consisting of arylene polyisocyanates such as tolylene, metaphenylene, 4-chlorophenylene-1,3-; methylene-bis-(phenylene-4-); bisphenylene-4,4'-; 3,3'-dimethoxy-biphenylene-4,4'-; 3,3'-diphenylbiphenylene-4,4'-; naphthalene-1,5- and tetrahydronaphthalene-1,5-diisocyanates and triphenylmethane triisocyanate; alkylene polyisocyanates such as ethylene, ethylidene; propylene-1,2-; butylene-1,4-; butylene-1,3-; hexylene-1,6-; decamethylene-1,10-; cyclohexylane-1,2-; cyclohexylene-1,4-; and methylene-bis(cyclohexyl-4,4'-) diisocyanates and mixtures thereof.

7. The process of claim 5 wherein the curing catalyst is selected from the group consisting of water, water containing an organic tin compound, an aqueous solution of alkali metal silicate containing 20 to 60% by weight of said alkali metal silicate, an aqueous solution of the organic silicate as produced in claim 1, containing 5 to 15% sodium hydroxide by weight and 20 to 60% of the organic silicate by weight, water containing 10 to 4% by weight of magnesium oxide and mixtures thereof.

8. The process of claim 5 wherein the curing catalyst is an aqueous solution of the organic silicate compound as produced in claim 1 which contains 5 to 15% by weight of an alkali metal hydroxide, selected from the group consisting of sodium hydroxide and potassium hydroxide, 20 to 60% by weight of the said organic silicate compound and 10 to 40% by weight of a polyol.

9. The process of claim 1 wherein additional steps are taken following step (d) of claim 1 to produce poly(urethane silicate) solid/fine cellular product by the following steps:
 (e) adding an organic silicate compound as produced in claim 1 to an aqueous solution containing 5 to 15% by weight of an alkali metal hydroxide, selected from the group consisting of sodium hydroxide and potassium hydroxide, until the aqueous solution contains 20 to 60% of said organic silicate compound, thereby
 (f) producing an aqueous solution of said organic silicate;
 (g) adding 10 to 200% by weight of said aqueous solution of organic silicate, percentage based on weight of the reactants, to an isocyanate-terminated liquid polyurethane prepolymer; then
 (h) mixing thoroughly, thereby
 (i) producing poly(urethane silicate) solid/fine cellular solid product.

10. The process of claim 9 wherein the isocyanate-terminated liquid prepolymer is selected from the group consisting of isocyanate-terminated polyester, isocyanate-terminated polyether, isocyanate-terminated polybutadiene, isocyanate-terminated polysulfide and mixtures thereof.

11. The process of claim 9 wherein a polyol is added in step (c) of claim 9 in the amount of 10 to 40% by weight, percentage based on the weight of the aqueous solution of organic silicate compound as produced in claim 9.

12. The process of claim 5 wherein a polyol is added in step (e) of claim 5 in the amount of 0.5 to 1 part by weight.

13. The process of claim 1 wherein additional steps are taken following step (d) of claim 1 to produce a polyisocyanate silicate solid/fine cellular solid product by the following steps:
 (e) adding an organic silicate compound as produced in claim 1 to an aqueous solution containing 5 to 15% by weight of an alkali metal hydroxide, selected from the group consisting of sodium hydroxide and potassium hydroxide until the aqueous solution contains 20 to 60% of said organic silicate compound, thereby
 (f) producing an aqueous solution of said organic silicate;
 (g) adding 10 to 200% by weight of said aqueous solution of organic silicate, percentage based on weight of the reactants, to a polyisocyanate, selected from the group consisting of arylene polyisocyanates, triphenylmethane triisocyanates, alkylene polyisocyanates, and mixtures thereof;
 (h) mixing thoroughly, thereby
 (i) producing polyisocyanate silicate solid/fine cellular solid product.

14. The process of claim 13 wherein a polyol is added in step (g) of claim 13 in the amount of 10 to 40% by weight, percentage based on the weight of the aqueous solution of organic silicate compound as produced in claim 13.

15. The product, polyisocyanate silicate solid/fine cellular solid, as produced by the process of claim 5.

16. The product, polyisocyanate silicate solid/fine cellular solid, as produced by the process of claim 13.

17. The product, polyurethane silicate solid/fine cellular product, as produced by the process of claim 9.

18. The process of claim 5 wherein the polyisocyanate is selected from the group consisting of 2,6-toluene diisocyanate, 2,4-toluene diisocyanate and mixtures thereof.

19. The process of claim 9 wherein resinous extender, in the amount of about 10 to 50% by weight, based on the weight of the polyurethane prepolymer, is added to the isocyanate-terminal liquid polyurethane prepolymer and selected from polyalpha-methylstyrene, mineral oil and coal tar.

20. The process according to claim 9 wherein 5 to 50%, based on the weight of the polyurethane prepolymer, of a high-boiling aromatic ester plasticizer is added to the isocyanate-terminal liquid polyurethane prepolymer.

* * * * *